United States Patent [19]

van Hoogstraten et al.

[11] 4,292,068

[45] Sep. 29, 1981

[54] HERBICIDAL METHOD

[75] Inventors: Samuel D. van Hoogstraten; David H. K. Davies, both of Cambridge, England

[73] Assignee: Fisons Limited, London, England

[21] Appl. No.: 99,723

[22] Filed: Dec. 4, 1979

[30] Foreign Application Priority Data

Dec. 16, 1978 [GB] United Kingdom ............... 48811/78

[51] Int. Cl.$^3$ ...................... A01N 43/08; A01N 43/12
[52] U.S. Cl. ........................................................ 71/88
[58] Field of Search ............................................ 71/88

[56] References Cited

U.S. PATENT DOCUMENTS 3,689,507  9/1972  Gates et al. ........................ 71/88 X

OTHER PUBLICATIONS

German Offen. 2,803,991 (Avg. 1978) Chem. Abst. vol 90 (1979) 6079n plus p. 936 of Chem. Subject Index See 5-benzoforand.

Primary Examiner—Catherine L. Mills
Attorney, Agent, or Firm—Wenderoth, Lind & Ponack

[57] ABSTRACT

The invention provides a method of combating rhizomatous and stoloniferous weeds by the application to a locus either infested or liable to infestation therewith an effective amount of 2,3-dihydro-3,3-dimethylbenzofuran-5-yl ethanesulphonate.

10 Claims, No Drawings

HERBICIDAL METHOD

This invention concerns a method of combating weeds.

In one aspect, this invention provides a method of combating rhizomatous or stoloniferous weeds as defined hereinafter, in which 2,3-dihydro-3,3-dimethylbenzofuran-5-yl ethanesulphonate is applied to a locus at which said weeds are growing, in an amount sufficient to exert its herbicidal effect.

The terms 'rhizomatous' and 'stoloniferous' are used herein to denote species of weeds which propagate by means of rhizomes and stolons respectively. Such species include *Cyperus esculentus* (yellow nutsedge), *Cyperus rotundus* (purple nutsedge), *Cyperus difformis, Cyperus iria, Sorghum halapense* (Johnsongrass), *Agropyron repens* (Couchgrass), *Pennisetum clandestinum* (Kikuyu grass), *Paspalum conjugatum* (Sour paspalum), *Paspalum distichum,* (knotgrass), *Oryza barthii, Imperata cylindrica* (cogongrass), *Oxalis corniculata* (creeping woodsorrel), *Cynodon dactylon* (bermudagrass), *Agrostis stolonifera, Brachiaria mutica, Carex lasiocarpa, Digitaria scalarum, Fimbristilis miliacea, Fimbristilis dichotoma, Phragmites australis, Muhlenbergia schreberi* and *Phalaris arundinacea.*

The present method is particularly effective against *Cyperus esculentus* and *Cyperus rotundus.*

At least partly because of their underground methods of propagation, rhizomatous and stoloniferous weeds tend to be highly resistant to conventional herbicides. Indeed, especially in relation to *Cyperus esculentus* and *Cyperus rotundus,* the existing treatments are very poor, giving only minimal control at high dosage rates. The present invention, we believe for the first time, provides a method whereby such weeds may be safely and economically controlled.

In the method of the present invention the active compound will normally be employed in the form of a composition, which can be prepared by admixing the ingredients. Usually the composition is initially produced in the form of a concentrate, e.g. containing 0.5–95%, preferably 20 to 80%, by weight of the active compound, and this is diluted with water or hydrocarbon, usually water, for application, generally such that the concentration of the compound is 0.05–5% by weight, although it may be considerably higher of course if ultra-low volume application techniques are employed.

The composition normally contains a surface active agent and/or a carrier.

The carrier may be a liquid, e.g. water (e.g. water used to dilute a concentrate for application). If water is employed as carrier in a concentrate, an organic solvent may also be present as carrier, though this is not usually employed. A surface active agent may advantageously be present.

The carrier may be a solid, which may be finely divided. Examples of suitable solids are limestone, clays, sand, mica, chalk, attapulgite, diatomite, perlite, sepiolite, silicas, silicates, lignosulphonates and solid fertilizers. The carrier can be of natural or synthetic origin or can be a modified natural material.

Wettable powders soluble or dispersible in water may be formed by admixing the compound in particulate form with a particulate carrier or spraying molten compound on to the particulate carrier, admixing a wetting agent and a dispersing agent and finely grinding the whole powder mixture.

An aerosol composition may be formed by admixing the compound with a propellant e.g. a polyhalogenated alkane such as dichlorodifluoromethane, and suitably also with a solvent.

A flowable suspension concentrate may be formed by grinding the compound with water, a wetting agent and a suspending agent (e.g. xanthan gum).

Thus the present composition can for example be solid (e.g. dust or granules) and contain a solid carrier, or liquid (e.g. an emulsifiable concentrate) and contain a liquid carrier which may for example be a ketone or a hydrocarbon (especially xylene) which boils within the range 130°–270° C.

The term 'surface active agent' is used in the broad sense to include materials variously called emulsifying agents, dispersing agents and wetting agents. Such agents are well known in the art.

The surface active agents used may comprise anionic surface active agents, for example mono- or di-esters of phosphoric acid with fatty alcohol ethoxylates or salts of such esters, fatty alcohol sulphates such as sodium dodecyl sulphate, ethoxylated fatty alcohol sulphates, ethoxylated alkylphenol sulphates, lignin sulphonates, petroleum sulphonates, alkylaryl sulphonates such as alkyl-benzene sulphonates or lower alkyl-naphthalene sulphonates, salts of sulphonated naphthalene-formaldehyde condensates, salts of sulphonated phenol-formaldehyde condensates, or more complex sulphonates such as the amide sulphonates, e.g. the sulphonated condensation product of oleic acid and N-methyl taurine or the dialkyl sulphosuccinates e.g. the sodium sulphonate of dioctyl succinate.

The surface active agents may also comprise non-ionic agents, for example condensation products of fatty acid esters, fatty alcohols, fatty acid amides or alkyl-substituted phenols with ethylene oxide, fatty esters of polyhydric alcohol ethers e.g. sorbitan fatty acid esters, condensation products of such esters with ethylene oxide e.g. polyoxyethylene sorbitan fatty acid esters, block copolymers of ethylene oxide and propylene oxide, acetylenic glycols such as 2,4,7,9-tetramethyl-5-decyn-4,7-diol, or ethoxylated acetylenic glycols.

The surface active agents may also comprise cationic agents, for example alkyl- and/or aryl-substituted quarternary ammonium compounds such as cetyl trimethylammonium bromide, or ethoxylated tertiary fatty amines.

Preferred surface active agents include ethoxylated fatty alcohol sulphates, lignin sulphonates, alkyl-aryl sulphonates, salts of sulphonated naphthalene-formaldehyde condensates, salts of sulphonated naphthalene-formaldehyde condensates, salts of sulphonated phenol-formaldehyde condensates, sodium oleoyl N-methyltauride, dialkyl sulphosuccinates, alkyl phenol ethoxylates, and fatty alkyl ethoxylates.

The present active compound may be admixed with or used in sequence with another pesticide, e.g. herbicide, insecticide or fungicide, or with a plant growth regulant or with a fertilizer. Particular advantages are obtained with mixtures or sequences with a second herbicide, especially trifluralin, dinitramine, fluometuron, pendimethalin, propachlor, alachlor, nitralin, 1-methyl-3-phenyl-5-(3-trifluoromethylphenyl)-4-pyridone or 5-(2-chloro-4-trifluoromethyl-phenoxy)-2-nitrobenzoic acid (acifluorfen) or a salt thereof (e.g. the sodium salt), but also bentazon, perfluidone, benfluralin, chlorthal dimethyl, diethatyl-ethyl, DSMA, MSMA, glyphosate, dacthal, diphenamid, ethalfluralin, fluridone, profluralin, butralin, methazole, metolachlor, dinoseb, fluchloralin, bifenox, desmetryne, cyanazine, tetrafluoron, norflurazon, oxadiazon, pebulate, perfluidone, prodiamine, profluralin, vernolate, prometryne, diuron, chlorobromuron, cyperquat, ethalfluralin, isopropalin, naproxamide, metobromuron, methazole; $N^1,N^1$dipropyl-2,6-dinitro-4-trifluoromethyl-m-phenylenediamine; N-chloroacetyl-2,6-dimethylanilinoacetaldehyde-ethyleneacetal; N-chloroacetyl-N-(2,6-diethylphenyl)glycine ethyl ester; N-chloroacetyl-N-(2-methyl-6-ethylphenyl)-glycine isopropyl ester; α-ethyl-N,N,4-trimethyl-3-phenylpyrazole-1-acetamide; O-methyl-O-(4-methyl-2-nitrophenyl) (1-methylethyl)phosphoramidothioate; 1-(3-trifluoromethylphenyl)-3-chloro-4-chloromethyl-2pyrrolid pyrrolidone; 1-[3-trifluoromethylbenzylideneamino]hydantoin; N-(3,4-dichlorophenyl)-N'-methyl-N'-thioisopropylurea; 2-chloro-1-(3-ethoxy-4-nitrophenoxy)-4-trifluoromethylbenzene; 3-(3,4-dichlorophenyl)-3-ethoxyallyl-1,1-dimethylurea; 2-[1-(2,5-dimethylphenyl)ethylsulphonyl]pyridine N-oxide; N-methyl-N-t-butylthiomethyl-N-(3-trifluoromethyl-phenyl)urea; 3-chloroacetyl-4,4-cyclohexanespiro(2,2-dimethyl-1,3-oxazolidine); EPTC; 3-amino-3-(4-bromophenylamino)-2-cyano-propenamide; 3-amino-3-(4-chlorophenylamino)-2-cyanopropenamide, 3-amino-3-(4-chloro-3-methylphenylamino)-2-cyanopropenamide, ethyl 3-amino-2-cyano-3-(N-methylphenylamino)propenoate; or isopropyl 3-amino-2-cyano-3-(N-methylphenylamino)-propenoate.

The ratio by weight of the present active compound to the second herbicide may vary over a wide range according to the particular compounds employed. In general, however, the ratio by weight of the present compound to the second herbicidal component will be from 10:1 to 1:15, more preferably from 5:1 to 1:5, and especially from 3:1 to 1:3.

The present compound may, if desired, be employed in admixture with non-phytotoxic oils.

The locus to which the present active compound is applied may be any locus where rhizomatous or stoloniferous weeds are growing. It is of especial use as a selective herbicide in crops, e.g. cotton, rubber, coffee, tea, cacao, ryegrass, safflower, sorghum, millets, mango, papaya, apples, pears, oranges, lemons, pineapples, bananas, yams, cassava, oilseed rape, jute, sunflowers, tobacco, cereals, red beet, sugar beet, sugar cane, cabbages, leeks, lettuce, peas, beans (e.g. navy beans, soya beans, french beans, runner beans and field beans), carrots, parsnips, parsley, onions, peanuts, maize, rice, sweet potatoes, or potatoes. Use in cotton, peanuts or tobacco is particularly advantageous. It may be applied pre- or post-planting of the crop, and is most preferably applied pre-emergence. If desired, however, it may be employed post-emergence.

The present active compound is preferably applied in an amount of from 0.1 to 20 kg/ha, more preferably 0.25 to 5 kg/ha, especially 0.5 to 2 kg/ha, when applied alone, and at about half these rates when applied in admixtures. The compound is preferably soil incorporated in cases where expected rainfall is low.

The invention will now be further described, though only by way of illustration, in the following Examples.

EXAMPLE 1

The treatments listed below were incorporated 1½" deep in plots (4 plots per treatment) in which cotton was then planted. Control of yellow nutsedge (*Cyperus esculentus*) was evaluated 26 days later relative to a control (0%).

The results obtained were as follows:

| Compound | Rate (kg/ha) | Mean % control |
|---|---|---|
| 2,3-dihydro-3,3-dimethylbenzofuran-5-yl ethanesulphonate | 1.0 | 77.5 |
| 2,3-dihydro-3,3-dimethylbenzofuran-5-yl ethanesulphonate | 2.0 | 71.25 |
| 2,3-dihydro-3,3-dimethylbenzofuran-5-yl ethanesulphonate | 4.0 | 77.5 |
| Perfluidone | 2.5 | 35.0 |
| Norflurazon | 2.0 | 45.0 |

All the above treatments were safe to the crop, exhibiting no significant phytotoxicity.

EXAMPLE 2

The treatments listed below were applied post-emergence to rice (3 plots per treatment) in 200 liters/hectare. Yellow nutsedge was also present in the plots but was treated pre-emergence. Control of this weed 42 days later relative to an untreated control (0%) was evaluated.

The results obtained were as follows:

| Compound | Rate (kg/ha) | Mean % control |
|---|---|---|
| 2,3-dihydro-3,3-dimethyl-benzofuran-5-yl ethanesulphonate | 1.0 | 71.6 |
| 2,3-dihydro-3,3-dimethyl-benzofuran-5-yl ethanesulphonate | 2.0 | 88.3 |
| 2,3-dihydro-3,3-dimethyl-benzofuran-5-yl ethanesulphonate | 3.0 | 93.3 |
| Bifenox | 1.0 | 0 |
| Bifenox | 2.0 | 0 |

All the above treatments were safe to the crop, exhibiting no significant pytotoxicity.

EXAMPLE 3

The treatments listed below were applied pre- or post-emergence (as indicated) to cotton (4 plots per treatment), the pre-emergence treatments being incorporated 3" deep after spraying at a rate of 200 liters/ha. Post-emergence treatments were sprayed in 200 liters/ha when the cotton had two true leaves. The pre-emergence treatments were evaluated for control of purple nutsedge (*Cyperus rotundus*) 8 weeks after application, and the post-emergence treatments were evaluated after 6 weeks.

Percentage control of purple nutsedge relative to untreated plots (0%) was as follows:

| Compound | Rate (kg/ha) | Pre-/Post-emergence | Mean % Control |
|---|---|---|---|
| 2,3-dihydro-3,3-dimethylbenzofuran-5-yl ethanesulphonate | 1.0 | Pre- | 57.5 |
| 2,3-dihydro-3,3-dimethylbenzofuran- | | | |

-continued

| Compound | Rate (kg/ha) | Pre-/Post-emergence | Mean % Control |
|---|---|---|---|
| 5-yl ethanesulphonate 2,3-dihydro-3,3-dimethylbenzofuran- | 2.0 | Pre- | 80.0 |
| 5-yl ethanesulphonate | 4.0 | Pre- | 82.5 |
| Perfluidone | 2.5 | Pre- | 11.2 |
| 2,3-dihydro-3,3-dimethyl-benzofuran-5-yl ethanesulphonate | 2.0 | Post- | 58.7 |
| DSMA | 2.8 | Post- | 48.7 |

All the above treatments were safe to the crop, exhibiting no significant phytotoxicity.

EXAMPLE 4

The following treatments with 2,3-dihydro-3,3-dimethylbenzofuran-5-yl ethanesulphonate were applied by spraying in the greenhouse, pre or post-emergence of the weeds as indicated. The results obtained relative to an untreated control in each case were as follows:

| Weed | Rate (kg/ha) | Pre/Post emergence | Mean % control |
|---|---|---|---|
| Pennisetum clandestinum | 2.0 | Pre | 100 |
| " | 4.0 | Pre | 100 |
| " | 2.0 | Post | 70 |
| " | 4.0 | Post | 90 |
| Paspalum distichum | 2.0 | Pre | 100 |
| " | 4.0 | Pre | 100 |
| " | 2.0 | Post | 60 |
| " | 4.0 | Post | 90 |
| Agropyron repens | 2.0 | Pre | 100 |
| " | 4.0 | Pre | 100 |
| " | 2.0 | Post | 95 |
| " | 4.0 | Post | 95 |
| Cyperus rotundus | 2.0 | Pre | 87 |
| " | 4.0 | Pre | 90 |
| Cyperus esculentus | 2.0 | Pre | 100 |
| " | 4.0 | Pre | 100 |
| Sorghum halapense | 4.0 | Pre | 57 |
| Cynodon dactylon | 4.0 | Pre | 40 |
| Oryza barthii | 4.0 | Post | 35 |

We claim:

1. A method of combating rhizomatous or stoloniferous weeds, in which 2,3-dihydro-3,3-dimethylbenzofuran-5-yl ethanesulphonate is applied to a locus at which said weeds are growing or are liable to grow, in an amount sufficient to exert its herbicidal effect.

2. A method according to claim 1 wherein the 2,3-dihydro-3,3dimethylbenzofuran-5-yl ethanesulphonate is applied in the form of a composition containing from 0.05 to 5% by weight thereof in association with a surface active agent and/or a carrier.

3. A method according to claim 1 wherein the 2,3-dihydro-3,3-dimethylbenzofuran-5-yl ethanesulphonate is applied in an amount of from 0.1 to 20 kg per hectare.

4. A method according to claim 3 wherein the 2,3-dihydro-3,3-dimethylbenzofuran-5-yl ethanesulphonate is applied in an amount of from 0.5 to 5 kg per hectare.

5. A method according to claim 4 wherein the 2,3-dihydro-3,3-dimethylbenzofuran-5-yl ethanesulphonate is applied in an amount of from 1 to 2 kg per hectare.

6. A method according to claim 1 wherein the rhizomatous or stoloniferous weeds which are combated are or include
Cyperus esculentus, Cyperus rotundus, Cyperus difformis, Cyperus iris, Sorghum halapense, Agropyron repens, Pennisetum clandestinum, Paspalum conjugatum, Paspalum distichum, Oryza barthii, Imperata cylindrica, Oxalis corniculata, Cynodon dactylon, Brachiaria mutica, Carex lasiocarpa, Digitaria scalarum, Fimbristilis miliacea, Fimbristilis dichotoma, Phragmites australis, Muhlenbergia schreberi or Phalaris arundinacea.

7. A method according to claim 1 wherein the locus to which 2,3-dihydro-3,3-dimethylbenzofuran-5-yl ethanesulphonate is applied is a locus where a crop is growing or is to grow.

8. A method according to claim 7 wherein the crop is cotton, rubber, coffee, tea, cacao, ryegrass, safflower, sorghum, millets, mango, papaya, apples, pears, pineapples, bananas, yams, cassava, oilseed rape, sunflowers, tobacco, a cereal, red beet, sugar beet, sugar cane, cabbages, leeks, lettuce, peas, beans, carrots, parsnips, onions, peanuts, maize, rice, sweet potatoes or potatoes.

9. A method according to claim 8 wherein the 2,3-dihydro-3,3-dimethylbenzofuran-5-yl ethanesulphonate is applied to a cotton crop to combat Cyperus esculentus and/or Cyperus rotundus.

10. A method according to claim 7 wherein the 2,3-dihydro-3,3-dimethylbenzofuran-5-yl ethanesulphonate is applied pre-emergence of the crop.

* * * * *